(12) United States Patent
Verschueren

(10) Patent No.: US 10,314,781 B2
(45) Date of Patent: Jun. 11, 2019

(54) NEBULIZER, A CONTROL UNIT FOR CONTROLLING THE SAME, AND A METHOD OF CONTROLLING A NEBULIZER

(75) Inventor: Alwin Rogier Martijn Verschueren, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 691 days.

(21) Appl. No.: 13/881,433

(22) PCT Filed: Oct. 25, 2011

(86) PCT No.: PCT/IB2011/054758
§ 371 (c)(1),
(2), (4) Date: Jun. 14, 2013

(87) PCT Pub. No.: WO2012/056398
PCT Pub. Date: May 3, 2012

(65) Prior Publication Data
US 2014/0145000 A1 May 29, 2014

(30) Foreign Application Priority Data
Oct. 29, 2010 (EP) .................................. 10189405

(51) Int. Cl.
*B05B 17/00* (2006.01)
*A61K 9/00* (2006.01)
(Continued)

(52) U.S. Cl.
CPC .......... *A61K 9/0078* (2013.01); *A61M 11/005* (2013.01); *B05B 17/0607* (2013.01);
(Continued)

(58) Field of Classification Search
CPC .... B05B 1/08; B05B 3/04; B05B 7/12; B05B 15/00; B05B 1/02; B05B 1/14;
(Continued)

(56) References Cited

U.S. PATENT DOCUMENTS 5,487,378 A * 1/1996 Robertson ......... A61M 15/0065
128/200.14
5,530,370 A 6/1996 Langhof et al.
(Continued)

FOREIGN PATENT DOCUMENTS

EP 1219314 7/2002
EP 1344545 9/2003
(Continued)

OTHER PUBLICATIONS

Dhand R. et al., "Aerosol Delivery During Mechanical Ventilation: From Basic Techniques to New Devices" Journal of Aerosol Medicine and Pulmonary Drug Delivery, Published in vol. 21 Issue 1: Mar. 8, 2008, pp. 45-60.

*Primary Examiner* — Arthur O Hall
*Assistant Examiner* — Christopher R Dandridge
(74) *Attorney, Agent, or Firm* — Michael W. Haas

(57) ABSTRACT

A control unit for controlling the operation of a nebulizer is provided that is configured to measure the impedance of an actuator in the nebulizer and to determine whether a nebulizing element in the nebulizer is positioned correctly with respect to the actuator on the basis of the measured impedance. Also provided is a nebulizer comprising a reservoir chamber for storing a liquid to be nebulized, an actuator for vibrating liquid stored in the reservoir chamber, and a control unit as described above.

14 Claims, 6 Drawing Sheets

(51) Int. Cl.
*A61M 11/00* (2006.01)
*B05B 17/06* (2006.01)

(52) U.S. Cl.
CPC ............... *A61M 2205/3317* (2013.01); *A61M 2205/702* (2013.01); *B05B 17/0638* (2013.01)

(58) Field of Classification Search
CPC .......... B05B 1/30; B05B 17/04; B05B 17/06; B05B 17/0607; B05B 17/0615; B05B 17/0623; B05B 17/063; B05B 17/0638; B05B 17/0646; B05B 17/0653; A01G 27/00; A61M 15/00; A61M 15/001; A61M 15/0001; A61M 15/005; A61M 15/0085; H01L 41/042
USPC ....... 239/67, 68, 70, 102.1, 102.2, 397, 413; 128/200.14, 200.16
See application file for complete search history.

(56) References Cited

U.S. PATENT DOCUMENTS

| | | | |
|---|---|---|---|
| 6,530,370 B1 | 3/2003 | Heinonen | |
| 6,539,937 B1* | 4/2003 | Haveri | A61M 15/0085 128/200.14 |
| 7,779,831 B1* | 8/2010 | Von Hollen | A61M 11/005 128/200.16 |
| 9,155,847 B2 | 10/2015 | Maeda | |
| 2003/0196660 A1 | 10/2003 | Havari | |
| 2004/0031488 A1* | 2/2004 | Terada | A61M 11/005 128/203.15 |
| 2007/0277816 A1 | 12/2007 | Morrison et al. | |
| 2008/0156320 A1 | 7/2008 | Low | |
| 2008/0173729 A1* | 7/2008 | Weng et al. | 239/102.2 |
| 2009/0114737 A1* | 5/2009 | Yu et al. | 239/69 |
| 2009/0200397 A1 | 8/2009 | Sheiman | |
| 2010/0122696 A1 | 5/2010 | Weng | |
| 2013/0079733 A1* | 3/2013 | Burt | B05B 7/0012 604/290 |

FOREIGN PATENT DOCUMENTS

| | | |
|---|---|---|
| JP | H04100557 A | 4/1992 |
| JP | H08196965 A | 8/1996 |
| JP | 2010213920 A | 9/2010 |
| WO | WO0228459 A1 | 4/2002 |

* cited by examiner

101 — Measure the impedance of the piezoelectric element in the nebuliser

103 — Determine whether a nebulising element in the nebuliser is positioned correctly on the basis of the measured impedance 105 — Is nebulising element positioned correctly?

107 — Initiate or continue operation of the nebuliser

FIG. 6A

109 — Prevent or cease operation of the nebuliser

111 — Notify a user of the nebuliser that the nebulising element needs to be repositioned

FIG. 6B

```
                    ( A )
                      │
                      ▼
201 ─ Operate the piezoelectric element
      at a first frequency of vibration
                      │
                      ▼
203 ─ Measure the impedance of the piezoelectric
      element operating at the first frequency of vibration
                      │
                      ▼
         ╱ Is measured         ╲
205 ─   ╱  impedance equal to,  ╲   No
       ╱ or within a predetermined range of, ╲────( B )
        ╲    a desired impedance    ╱
         ╲      value?             ╱
                      │ Yes
                      ▼
207 ─ Operate the piezoelectric element at a
      second frequency of vibration
                      │
                      ▼
209 ─ Measure the impedance of the piezoelectric element
      operating at the second frequency of vibration
                      │
                      ▼
         ╱ Is measured         ╲
211 ─   ╱ impedance equal to, or ╲   No
       ╱ within a predetermined range of, ╲───( B )
        ╲ a predeermined impedance ╱
         ╲      value?            ╱
                      │ Yes
                      ▼
213 ─ Initiate or continue operation of the nebuliser
```

FIG. 7

NEBULIZER, A CONTROL UNIT FOR CONTROLLING THE SAME, AND A METHOD OF CONTROLLING A NEBULIZER

TECHNICAL FIELD OF THE INVENTION

The invention relates to a nebulizer that nebulizes a liquid stored therein into fine droplets, for example for inhalation by a user of the nebulizer, and in particular relates to a control unit for a nebulizer and a method of controlling a nebulizer that can detect whether a nebulizing element, such as a mesh or membrane, is positioned correctly in the nebulizer.

BACKGROUND TO THE INVENTION

Nebulizers, or atomizers as they are sometimes called, are devices that generate a fine spray or aerosol from a liquid. A particularly useful application for nebulizers is to provide a fine spray containing a dissolved or a suspended particulate drug for administration to a patient by inhalation.

Piezo-mesh based nebulizers are commonly used to generate aerosols in such drug delivery apparatus, whereby a piezoelectric element vibrates a mesh to produce the fine aerosol spray. In particular, droplets dispensed on the mesh are vibrated by the piezoelectric element to create the spray. In some nebulizers the piezoelectric element is bonded to a mesh element, whereas in other nebulizers the mesh element is separate from (i.e. not in contact with) the piezoelectric element (sometimes referred to as piezo-cavity-mesh based nebulizers). An advantage of having the mesh element separate from the piezoelectric element is that the mesh element can be removed from the nebulizer and cleaned or entirely replaced after a certain amount of use.

SUMMARY OF THE INVENTION

However, it has been found that the performance of the nebulizer, which can be measured in terms of the droplet generation rate, is very sensitive to the separation between the piezoelectric element and the mesh in the nebulizer. In particular, the size of the liquid cavity between the piezoelectric element and the mesh influences the pressure at the mesh, and thereby the droplet generation rate.

FIG. 1 illustrates the pressure generated at a mesh in a nebulizer for various frequencies of vibration for a piezoelectric element and various distances between the piezoelectric element and the mesh (also referred to as water height). Thus, it can be seen that a deviation of just tens of microns (tens of micrometers) from an optimum position can have a significant impact on the pressure at the mesh, and therefore on the droplet generation rate.

Therefore, consistent performance of the nebulizer relies on the accurate repositioning of the mesh in the nebulizer after cleaning or replacement. Moreover, if the mesh is not repositioned correctly, the nebulizer may not function at all or components of the nebulizer may be damaged during operation.

Thus, there is a need for a control unit for a nebulizer and a method of controlling a nebulizer that can detect whether the mesh has been positioned correctly.

According to a first aspect of the invention, there is provided a control unit for controlling the operation of a nebulizer, wherein the control unit is configured to measure the impedance of an actuator in the nebulizer and to determine whether a nebulizing element in the nebulizer is positioned correctly with respect to the actuator on the basis of the measured impedance.

In one embodiment, the control unit is configured to determine that the nebulizing element is positioned correctly if the measured impedance of the actuator is equal to or within a predetermined range of a predetermined impedance value.

In an alternative embodiment, the control unit is configured to measure the impedance of the actuator when the actuator is operating at first and second frequencies, and to determine that the nebulizing element is positioned correctly if both of the measured impedances are equal to or within a predetermined range of respective predetermined impedance values. This embodiment can prevent false-positive errors in the determination of the position of the nebulizing element.

Preferably, the control unit is configured to activate the actuator to nebulize liquid if it is determined that the nebulizing element is positioned correctly in the nebulizer. In this way, the nebulizer will be operated at an optimum or near-optimum droplet generation rate.

In one implementation, the control unit is configured to deactivate the actuator if it is determined that the nebulizing element is not positioned correctly. In this way, it is possible to avoid any of the components of the nebulizer being damaged through the incorrect positioning of the nebulizing element.

In a further implementation, the control unit is configured to provide an indication to a user of the nebulizer that the nebulizing element needs to be repositioned by the user.

According to one embodiment, the control unit is configured to adjust a frequency of vibration of the actuator if it is determined that the nebulizing element is not positioned correctly.

According to another embodiment, the control unit is configured to adjust the relative position of the actuator and nebulizing element using a second actuator in the nebulizer if it is determined that the nebulizing element is not positioned correctly.

Preferably, the control unit is configured to re-measure the impedance of the actuator after the adjustments described above to determine if operation of the nebulizer can be permitted.

In one embodiment, the control unit is configured to measure the impedance of the actuator by applying a sinusoidal voltage with a known amplitude to the actuator and measuring the amplitude of the resulting current and the phase shift between the resulting current and the applied voltage.

According to an alternative embodiment, the control unit is configured to measure the impedance of the actuator by measuring the voltage across the actuator and current through the actuator during operation.

According to a second aspect of the invention, a nebulizer is provided that comprises a reservoir chamber for storing a liquid to be nebulized; an actuator for vibrating liquid stored in the reservoir chamber; and a control unit as described above.

Preferably, the nebulizer further comprises a nebulizing element positioned in the reservoir for nebulizing the liquid when the actuator vibrates the liquid, and, even more preferably, the nebulizing element is removable from the nebulizer.

According to a third aspect of the invention, there is provided a method of controlling a nebulizer, the method comprising:

measuring the impedance of an actuator in the nebulizer; and determining whether a nebulizing element in the nebulizer is positioned correctly with respect to the actuator on the basis of the measured impedance.

In one embodiment, the nebulizing element is determined to be positioned correctly if the measured impedance of the actuator is equal to or within a predetermined range of a predetermined impedance value.

In an alternative embodiment, the step of measuring the impedance of the actuator comprises measuring the impedance of the actuator at first and second frequencies, and wherein the step of determining comprises determining that the nebulizing element is positioned correctly if both of the measured impedances are equal to or within a predetermined range of respective predetermined impedance values.

Preferably, the method further comprises the step of activating the actuator to nebulize liquid if it is determined that the nebulizing element is positioned correctly in the nebulizer.

In one implementation, the method further comprises the step of deactivating the actuator if it is determined that the nebulizing element is not positioned correctly. Preferably, in this implementation, the method further comprises providing an indication to a user of the nebulizer that the nebulizing element needs to be repositioned by the user.

In one embodiment, the method further comprises the step of adjusting a frequency of vibration of the actuator if it is determined that the nebulizing element is not positioned correctly.

In another embodiment, the method further comprises the step of adjusting the relative position of the actuator and nebulizing element using a second actuator in the nebulizer if it is determined that the nebulizing element is not positioned correctly.

Preferably, the method further comprises the step of re-measuring the impedance of the actuator after the step of adjusting.

In one embodiment, the step of measuring the impedance of the actuator comprises applying a sinusoidal voltage with a known amplitude to the actuator and measuring the amplitude of the resulting current and the phase shift between the resulting current and the applied voltage.

In another embodiment, the step of measuring the impedance of the actuator comprises measuring the voltage across the actuator and current through the actuator during operation.

According to a fourth aspect of the invention, there is provided a computer program product comprising a computer readable medium having computer program code embodied therein, the computer program code comprising code that, when executed by a computer or processor, is configured to cause the computer or processor to perform the steps in any of the methods described above.

According to a fifth aspect of the invention, there is provided a control unit for controlling the operation of a nebuliser, wherein the control unit is configured to operate the nebuliser at a non-resonant frequency thereof to provide a required or maximum output rate of nebulised liquid.

A nebuliser can be provided that comprises a control unit as described in the fifth aspect; a reservoir chamber for storing a liquid to be nebulised; and an actuator for causing liquid stored in the reservoir chamber to be nebulised. The nebuliser may further comprise a nebulising element positioned in the reservoir for nebulising the liquid when the actuator is activated.

According to a sixth aspect of the invention, there is provided a method of controlling a nebuliser that comprises operating the nebuliser at a non-resonant frequency thereof to provide a required or maximum output rate of nebulised liquid.

In the fifth and sixth aspects of the invention above, it will be appreciated that the resonant frequency of the nebuliser corresponds to the frequency at which maximum power transfer occurs in the nebuliser (i.e. the frequency at which the impedance is a minimum).

BRIEF DESCRIPTION OF THE DRAWINGS

Exemplary embodiments of the invention will now be described, by way of example only, with reference to the following drawings, in which:

FIGS. 6A-6D are flow charts illustrating a method of controlling a nebulizer according to an embodiment of the invention; and FIG. 7 is a flow chart illustrating an alternative method of controlling a nebulizer according to an embodiment of the invention.

DETAILED DESCRIPTION OF THE PREFERRED EMBODIMENTS

Figure 2:
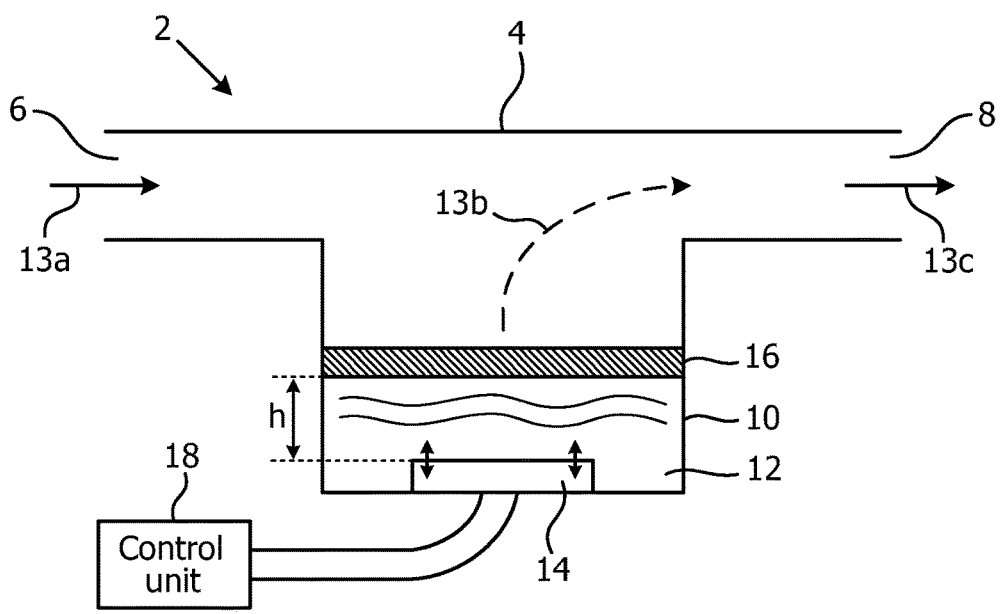
FIG. 2 is a block diagram of a nebulizer according to an embodiment of the invention.

A nebulizer 2 according to an embodiment of the invention is shown in FIG. 2. The nebulizer 2 comprises a body 4 having an inlet 6 and an outlet 8 arranged so that when a user of the nebulizer 2 inhales through the outlet 8, air is drawn into and through the nebulizer 2 via the inlet 6 and outlet 8 and into the user's body. In some embodiments, the outlet 8 is provided in the form of a mouthpiece or a facial or nasal mask. Alternatively, the outlet 8 can be configured to allow connection to a separate replaceable mouthpiece or facial or nasal mask.

A reservoir chamber 10 for storing a liquid 12, for example a medication or drug, to be nebulized (i.e. to be turned into a fine mist or spray) is provided in the body 4 of the nebulizer 2 between the inlet 6 and outlet 8. The nebulizer 2 is configured such that fine droplets of the nebulized liquid 12 combine with the air drawn through the nebulizer 2 when the user inhales to deliver a dose of the medication or drug to the user. This operation is illustrated by arrow 13a (which represents the air that is drawn into the nebulizer 2 through the inlet 6), arrow 13b (which represents the liquid nebulized from the reservoir chamber 10) and arrow 13c (which represents the air containing the nebulized liquid that is drawn out of the nebulizer 2 by the user through the outlet 8).

An actuator 14 for agitating or vibrating liquid 12 stored in the reservoir chamber 10 is provided in the reservoir chamber 10 along with a nebulizing element 16 for nebulizing the liquid 12 when the liquid 12 is vibrated. The actuator 14 is provided at, or proximate to, the bottom of the reservoir chamber 10, and the nebulizing element 16 is located in the reservoir chamber 10 above, and spaced from, the actuator 14. The nebulizing element 16 is spaced from the actuator 14 by a distance h, which is referred to as the 'water height' as the liquid 12 fills the reservoir chamber 10 up to the height of the nebulizing element 16. It will be appreciated that the liquid 12 in the reservoir chamber 10 will be depleted as the nebulizer 2 is operated, and more liquid 12 must be added to the reservoir chamber 10 to maintain the liquid 12 at the height h for the nebulizer 2 to continue operating. Therefore, the nebulizer 2 may comprise, or be coupled to, a further chamber (not shown in FIG. 2) that stores liquid for replenishing the liquid 12 in the reservoir chamber 10. The liquid from the further chamber may flow into the reservoir chamber 10 due to the action of gravity and capillary filling.

In the embodiments of the invention that are described further below, the actuator 14 is provided in the form of a piezoelectric element. However, those skilled in the art of nebulizers will appreciate that other forms of actuator 14 can be used in nebulizers according to the invention. It will also be appreciated that a piezoelectric element 14 can be covered with a plastic or metal cover layer to avoid direct contact between the piezoelectric element and the liquid 12.

In preferred embodiments of the invention, the nebulizing element 16 is in the form of a mesh or membrane having a plurality of small holes through which small amounts of the liquid can pass. In one specific embodiment, the mesh or membrane comprises in the region of 5000 2 μm holes through which droplets of liquid can pass when the actuator 14 is activated.

Referring again to FIG. 2, the nebulizer 2 further comprises a control unit 18 that includes circuitry for controlling the operation of the nebulizer 2. In particular, the control unit 18 is connected to the actuator 14 and activates and deactivates the actuator 14, as required.

In some embodiments, the control unit 18 is an integral component of the nebulizer 2 within the body 4 of the nebulizer 2. However, in alternative embodiments, the control unit 18 can be provided in a unit that is separate to, and even detachable from, the body 4 of the nebulizer 2.

As described above, obtaining consistent performance from a nebulizer 2 relies on the accurate repositioning of the nebulizing element 16 in the nebulizer 2 after cleaning or replacement. Furthermore, if the nebulizing element 16 is not repositioned correctly, the nebulizer 2 may not function at all or components of the nebulizer 2 may be damaged when operation is attempted. Therefore, in accordance with the invention, the control unit 18 is configured to determine whether the nebulizing element 16 is positioned correctly in the nebulizer 2, and in particular positioned correctly relative to the actuator 14.

Figure 1:
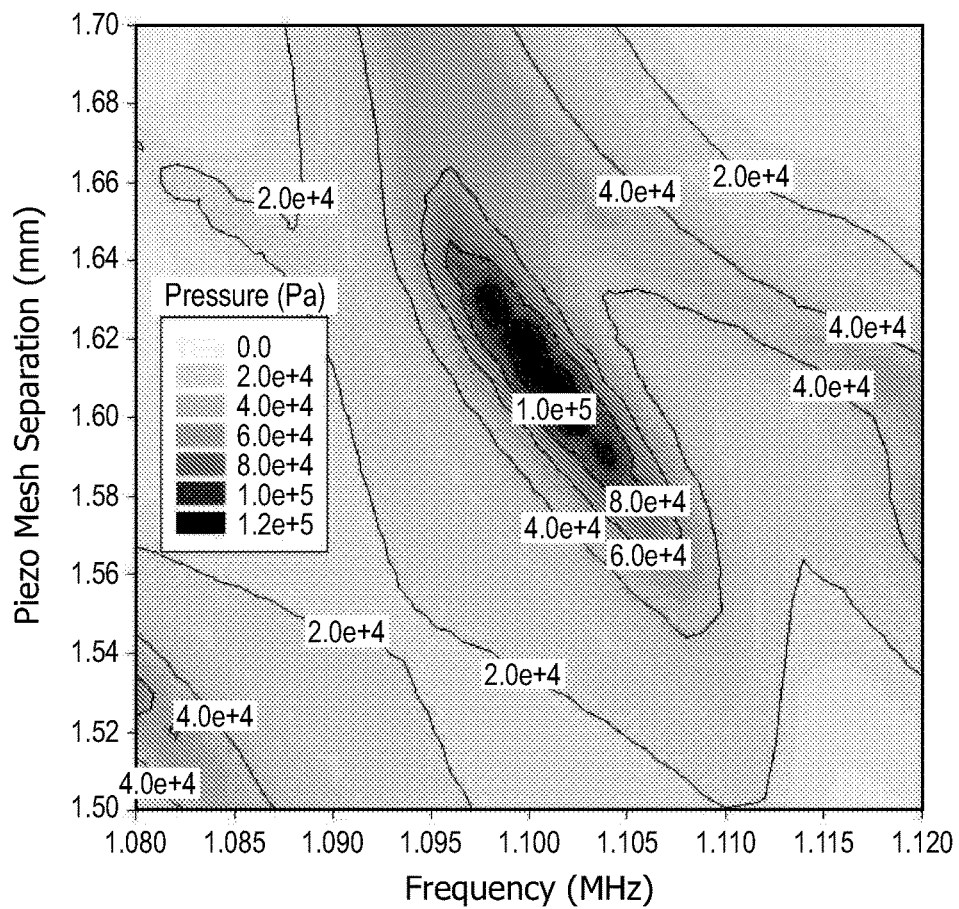
FIG. 1 shows the pressure at a mesh for various frequencies of vibration of a piezoelectric element and various distances between the piezoelectric element and the mesh.

As described above, FIG. 1 illustrates the pressure generated at a nebulizing element 16 in the nebulizer 2 for various frequencies of vibration for the piezoelectric element 14 and various distances between the piezoelectric element 14 and the nebulizing element 16, and it can be seen that a deviation of just tens of microns (tens of micrometers) from an optimum position can have a significant impact on the pressure at the nebulizing element 16, and therefore on the droplet generation rate.

Figure 3:
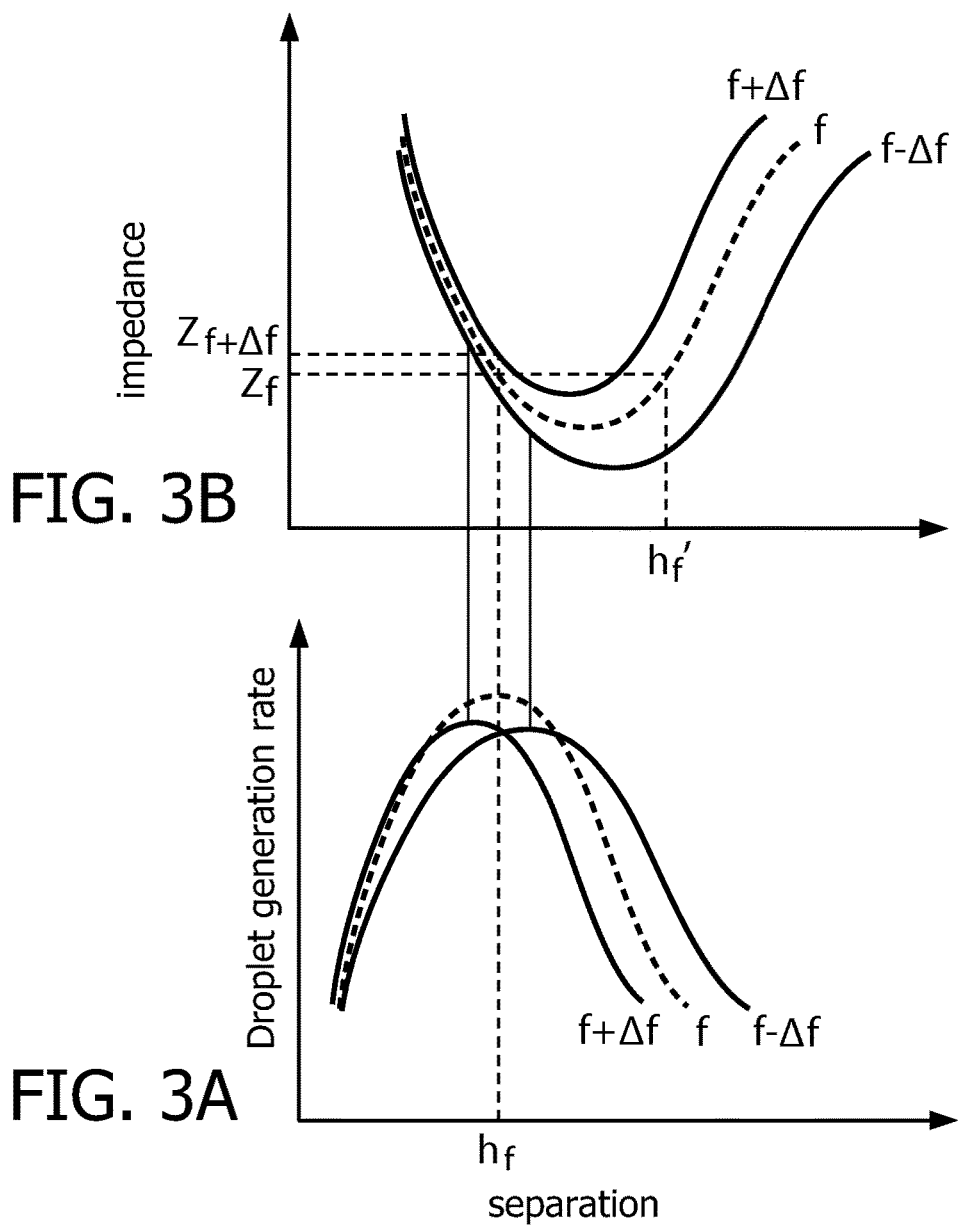
FIGS. 3A and B are graphs illustrating the variation in droplet generation rate and impedance of a piezoelectric element with changes in the separation between the piezoelectric element and a nebulizing element.

These results are illustrated in an alternative form in FIG. 3A shows the variation in the droplet generation rate with the distance between the piezoelectric element 14 and the nebulizing element 16 for three different frequencies of vibration for the piezoelectric element 14.

It has been found that the impedance of the piezoelectric element 14 in the nebulizer 2 (and more specifically the real part of the complex impedance of the piezoelectric element 14) is related to the position of the nebulizing element 16 in the nebulizer 2 relative to the piezoelectric element 14. These findings are illustrated in the combination of the graphs in FIGS. 3A and B, which share the same x-axis. Thus, it can be seen from FIG. 3B that the impedance of the piezoelectric element 14 varies with the separation between the piezoelectric element 14 and the nebulizing element 16 (and also with the frequency of operation of the piezoelectric element 14). It can also be seen that the impedance of the piezoelectric element 14 has a specific value when the droplet generation rate is optimal (and it will be noted that this impedance value is not a maximum or minimum value for the impedance, but an intermediate value). Therefore, according to the invention, a measurement of the impedance can be used to determine whether the nebulizing element 16 is positioned correctly in the nebulizer 2 (i.e. the nebulizing element 16 is in a position where optimal or near-optimal droplet generation performance is realized).

It will also be appreciated that the minimum value for the impedance occurs when the nebuliser 2 (particularly the reservoir chamber 10, piezoelectric element 14 and nebulising element 16) is in resonance, which occurs at a specific frequency where maximum energy is transferred (i.e. the power is at a maximum). Thus, it can be seen from FIGS. 3(a) and (b) that the optimal droplet generation rate corresponds to an intermediate value for the impedance, and therefore the optimal droplet generation rate is achieved by operating the nebuliser 2 at a frequency other than the resonant frequency (and thus where the impedance is not at a minimum and the power is not at a maximum).

In addition, it has been found that the optimal impedance value for the piezoelectric element 14 (i.e. the impedance value for the piezoelectric element 14 that corresponds to the correct positioning of the nebulizing element 16 in the nebulizer 2 relative to the piezoelectric element 14) is nebulizing element-specific, i.e. it varies for different types and/or configurations of nebulizing element 16. In this respect, the different types and/or configurations can relate to the material used to make the nebulizing element 16, the thickness of the nebulizing element 16 and the number and/or size of the holes in the nebulizing element 16. In some embodiments of the invention, the control unit 18 can be programmed with the appropriate impedance value for the nebulizing element 16 by a user of the nebulizer 2, or the control unit 18 can automatically obtain the information from an electronic data chip (not shown in FIG. 2) associated with the particular liquid (i.e. medication) in the reservoir chamber 10 and/or nebulizing element 16 (for example as used in the currently available Philips Respironics I-neb nebulizer).

Figure 4:
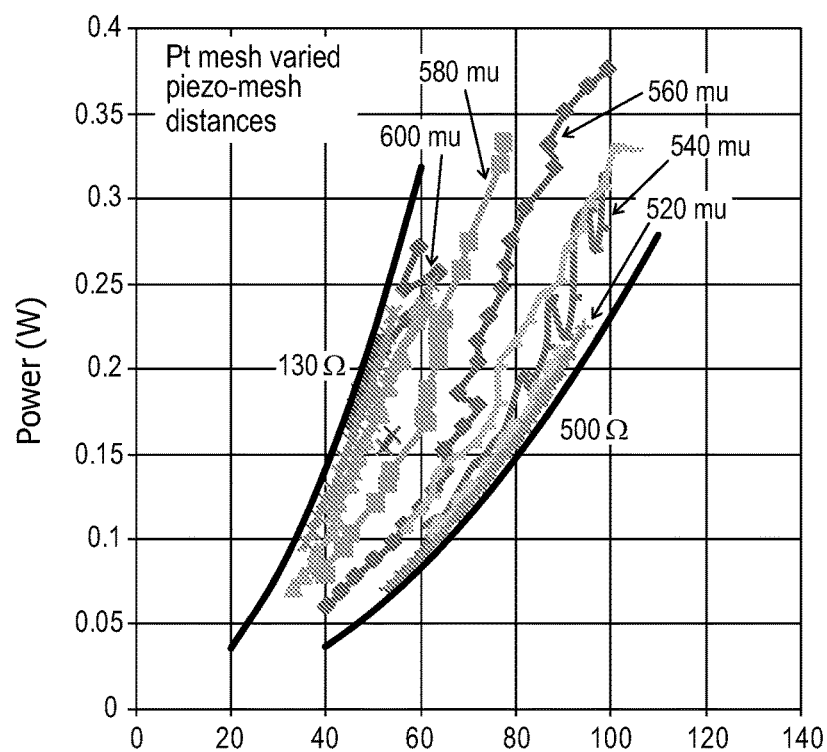
FIG. 4 is a graph illustrating how the power applied to a piezoelectric element changes with the peak-to-peak voltage across the piezoelectric element for various distances between the piezoelectric element and a nebulizing element.

The graph in FIG. 4 illustrates how the power (in Watts) applied to the piezoelectric element 14 changes with the peak-to-peak voltage (Vpp) across the piezoelectric element 14 for various distances between the piezoelectric element 14 and a platinum mesh having a particular thickness that is used as the nebulizing element 16.

In theory, for a voltage-independent impedance, the relation between power and voltage should be a quadratic function completely determined by the real part of the impedance. Experimentally, as shown in FIG. 4, quadratic relations are observed, from which impedance values between 130Ω and 500Ω were determined. Thus, FIG. 4 illustrates how the impedance of the piezoelectric element 14 depends on the distance between the piezoelectric element 14 and the platinum mesh 16.

Figure 5:
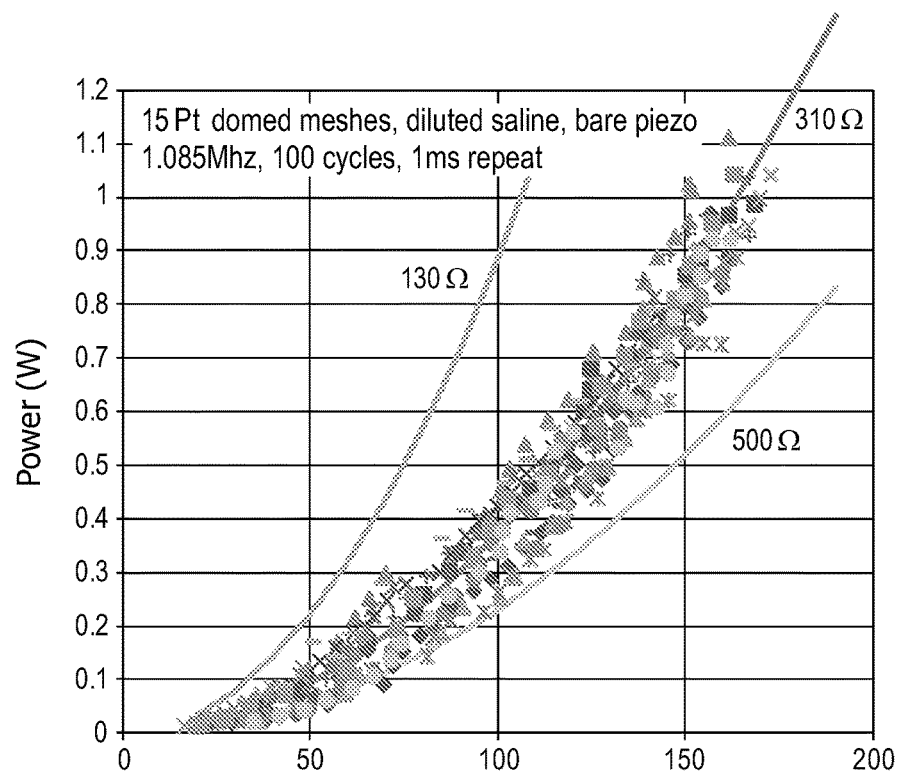
FIG. 5 is a graph illustrating how the power applied to a piezoelectric element changes with the peak-to-peak voltage across the piezoelectric element for various different platinum meshes that are each positioned in the correct position in the nebulizer.

The graph in FIG. 5 illustrates how the power (in Watts) applied to the piezoelectric element 14 changes with the peak-to-peak voltage (Vpp) across the piezoelectric element 14 for various (fifteen) different platinum meshes that are each positioned in the correct (optimal) position, or near optimal position, in the nebulizer 2. Thus, it can be seen from FIG. 5 that for maximum (or near-maximum) droplet generation for these platinum meshes, the impedance of the piezoelectric element 14 is a value at or around 310Ω.

As described above, the optimal impedance value for a particular nebulizing element 16 depends on the composition of the nebulizing element 16. For example, it has been found that meshes made of nickel-palladium (NiPd) exhibit similar behavior to the platinum meshes described above, but the optimum impedance value for those meshes was found to be 600Ω.

In general, the optimal impedance value for a particular nebulizing element 16 will be determined through testing prior to any use of that type of nebulizing element 16 in a nebulizer 2. Once an optimal impedance value has been determined, the value will be applicable to all other meshes produced from the same material and having the same geometry.

The operation of the control unit 18 in accordance with the invention will be described in more detail below with reference to FIGS. 6A-6D. The method described below can be initiated by the control unit 18 when a nebulizing element 16 is first positioned in the nebulizer 2, when a user tries to use the nebulizer 2 and/or during use of the nebulizer 2.

Firstly, referring to FIG. 6A, the operation according to the invention begins in step 101 in which the impedance of the piezoelectric element 14 in the nebulizer 2 is measured by the control unit 18. In particular, the control unit 18 measures the real part of the complex impedance of the piezoelectric element 14. It will be appreciated that this measurement is performed while liquid 12 is present in the reservoir chamber 10.

It will be appreciated that step 101 can be performed by the control unit 18 before the nebulizer 2 is activated (i.e. before sufficient current is provided to the piezoelectric element 14 to cause the liquid 12 to be nebulized), or during operation of the nebulizer 2 (i.e. when the piezoelectric element 14 is causing the liquid 12 to be nebulized).

In the first instance, the control unit 18 can apply a small sinusoidal voltage having a known amplitude $V_{amp}$ to the piezoelectric element 14 (the voltage being small in the sense that it is below the voltage required to cause the piezoelectric element 14 to nebulize the liquid 12) and measure the resulting current $I_{amp}$ and the phase shift $\varphi_{amp}$ between the applied voltage signal and the resulting current signal.

The control unit 18 can then calculate the real part of the impedance of the piezoelectric element 14 using:

$$\mathrm{Re}\{Z\} = \frac{V_{amp}}{I_{amp}}\cos\varphi \quad (1)$$

Alternatively, in the second instance described above (i.e. measuring the impedance during operation of the nebulizer 2), the control unit 18 can determine the impedance during operation for arbitrary driving signals. In this case, the control unit 18 determines the real part of the impedance of the piezoelectric element 14 from the voltage applied to the element 14 over time, V(t), and the measured current through the element 14 over time, I(t), using:

$$\mathrm{Re}\{Z\} = \frac{\int_{period} V(t) * V(t)dt}{\int_{period} V(t) * I(t)dt} \quad (2)$$

Once the impedance of the piezoelectric element 14 has been measured, the control unit 18 then uses the measured impedance value to determine whether the nebulizing element 16 is positioned correctly in the nebulizer 2 (step 103). Following an analysis such as that illustrated in FIG. 5 above, an optimal impedance value for the nebulizing element 16 that results in optimal or near-optimal droplet generation performance will be known before the nebulizing element 16 is positioned in the nebulizer 2. Therefore, in step 103 the control unit 18 can compare the measured impedance value to the known optimal impedance value to determine whether the nebulizing element 16 is positioned correctly in the nebulizer 2.

In one embodiment, the control unit 18 can determine that the nebulizing element 16 is positioned correctly if the measured impedance value is within a predetermined range of the optimal impedance value. It will be appreciated that the predetermined range can be specified in terms of being within a particular percentage value of the optimal impedance value (i.e. the measured impedance must be within, for example, 1%, 5% or 10% of the optimal impedance value for the control unit 18 to determine that the nebulizing element 16 is positioned correctly), or in terms of a particular range of impedance values around the optimal impedance value (i.e. for the platinum mesh described above, the predetermined range for determining correct positioning can be, for example, between 280Ω and 340Ω).

If the control unit 18 determines that the nebulizing element 16 is positioned correctly in the nebulizer 2 (steps 103 and 105) then the control unit 18 can initiate (or continue) operation of the nebulizer 2 by supplying a sufficient voltage signal to the piezoelectric element 14 (step 107). The control unit 18 allows operation of the nebulizer 2 until the user stops breathing through the nebulizer 2 or the required dosage of the medication or drug in the liquid has been nebulized.

If the control unit 18 determines that the nebulizing element 16 is not positioned correctly in the nebulizer 2 on the basis of the measured impedance (steps 103 and 105) then the control unit 18 takes further action, as described in more detail below.

In one implementation of the nebulizer 2, as illustrated in FIG. 6B, on determining that the nebulizing element 16 is not positioned correctly, the control unit 18 prevents or ceases operation of the nebulizer 2 (i.e. by not providing a voltage signal to the piezoelectric element 14), in order to prevent sub-optimal droplet generation performance, and to avoid any possible damage to the components of the nebulizer 2 (step 109).

The control unit 18 can then notify the user of the nebulizer 2 that the nebulizing element 16 is positioned incorrectly and needs to be repositioned before the nebulizer 2 can be operated properly. The control unit 18 may notify the user of this in any conventional manner, for example by initiating an audible alarm, warning signal or spoken message, and/or by providing a visual indication such as a warning light or LED, or by providing a written message or symbol on a display of the nebulizer 2 (not shown in FIG. 2).

If the user repositions the nebulizing element 16 in the nebulizer 2, the control unit 18 can return to step 101 and repeat the measurement of the impedance of the piezoelectric element 14. If that measurement indicates that the nebulizing element 14 is positioned correctly in the nebulizer 2, then the control unit 18 can initiate the operation of the nebulizer 2 as shown in step 107.

Figure 6C:
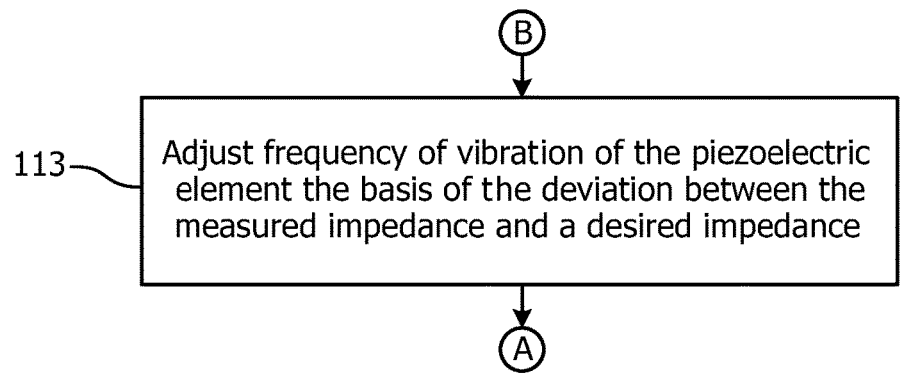

In an alternative implementation of the nebulizer 2, as illustrated in FIG. 6C, on determining that the nebulizing element 16 is not positioned correctly, the control unit 18 can adjust the voltage signal applied to the piezoelectric element 14 to change the frequency of vibration of the piezoelectric element 14, thereby improving the performance of the nebulizer 2 (step 113). In particular, as demonstrated by the graphs in FIGS. 1 and 3, as there is a correlation between the distance between the piezoelectric element 14 and the nebulizing element 16 (the water height) and the frequency at which the piezoelectric element 14 is vibrating, small deviations of the water height from the optimal value can be compensated by the control unit 18 adjusting the frequency of vibration of the piezoelectric element 14.

In one embodiment, the control unit 18 can adjust the frequency of vibration of the piezoelectric element 14 by an amount determined using the measured impedance value and a look-up table. In an alternative embodiment, the control unit 18 can adjust the frequency of vibration of the piezoelectric element 14 by an amount based on the magnitude of the difference between the measured impedance value and the optimal impedance value. In an another alternative embodiment, the control unit 18 can adjust the frequency of vibration of the piezoelectric element 14 by a fixed amount, regardless of the difference between the measured impedance value and the optimal value.

In the embodiments described in the paragraph above, the control unit 18 can then return to step 101 and re-measure the impedance of the piezoelectric element 14 to determine if operation of the nebulizer 2 can be permitted. If not, the control unit 18 can loop through steps 101, 103, 105 and 113 until the droplet generation performance of the nebulizer 2 reaches an acceptable value.

In one embodiment, since the frequency of vibration of the piezoelectric element 14 has changed, it is possible for the re-measuring step described to use a modified optimal impedance value. In the embodiment where a look-up table is used, it is possible for the look-up table to contain data corresponding to that shown in FIGS. 3A and 3B, which means that the control unit 18 uses the measured impedance to look up (i) the actual separation between the piezoelectric element 14 and nebulizing element 16, (ii) the optimal driving frequency, and (iii) the corresponding modified optimal impedance.

In some embodiments, if the control unit 18 determines that the adjustment of the frequency of vibration of the piezoelectric element 14 will not provide an acceptable droplet generation performance (for example based on the difference between the measured impedance value and the optimal impedance value exceeding a threshold or following one or more loops of steps 101, 103, 105 and 113 that do not result in the required performance being achieved), the control unit can then perform steps 109 and 111 and notify the user of the nebulizer 2 that the nebulizing element 16 needs to be manually repositioned in the nebulizer 2.

Figure 6D:
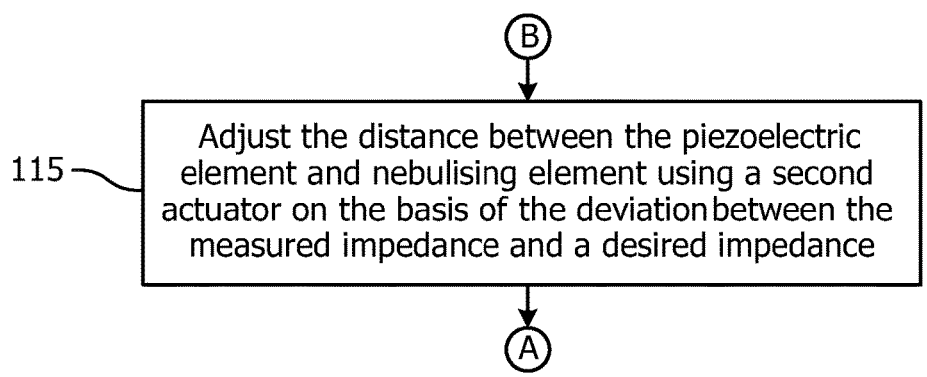

In yet another alternative implementation of the nebulizer 2, as illustrated in FIG. 6D, the control unit 18 can itself adjust the position of the nebulizing element 16 in the nebulizer 2 if it determines that the nebulizing element 16 is not positioned correctly in the nebulizer 2. In this embodiment the nebulizer 2 is provided with a further actuator that can be used to adjust the relative positions of the nebulizing element 16 and piezoelectric element 14 in the nebulizer 2. Preferably, the further actuator is configured to move the nebulizing element 16 in the nebulizer 2 under the control of the control unit 18, but it will be appreciated that in alternative implementations the further actuator can be used to move the piezoelectric element 14 instead. Those skilled in the art will be aware of suitable actuators that can be provided in a nebulizer 2 for moving the nebulizing element 16 or piezoelectric element 14, and therefore further details will not be provided herein.

On determining that the nebulizing element 16 is not positioned correctly, the control unit 18 can control the further actuator to adjust the relative position of the nebulizing element 16 relative to the piezoelectric element 14 (i.e. by moving the nebulizing element 16 closer to or further away from the piezoelectric element 14), thereby causing the impedance of the piezoelectric element 14 to approach the optimal impedance value and improving the performance of the nebulizer 2 (step 115 of FIG. 6D).

In one embodiment, the control unit 18 can control the further actuator to adjust the position of the nebulizing element 16 by an amount based on the magnitude of the difference between the measured impedance value and the optimal impedance value. In an alternative embodiment, the control unit 18 can control the further actuator to adjust the position of the nebulizing element 16 by a fixed amount, regardless of the difference between the measured impedance value and the optimal value.

In both embodiments described in the paragraph above, the control unit 18 can then return to step 101 and re-measure the impedance of the piezoelectric element 14 to determine if operation of the nebulizer 2 can be permitted. If not, the control unit 18 can loop through steps 101, 103, 105 and 115 until the droplet generation performance of the nebulizer 2 reaches an acceptable value.

In some embodiments, if the control unit 18 determines that the adjustment of the position of the nebulizing element 16 will not provide an acceptable droplet generation performance (for example based on the difference between the measured impedance value and the optimal impedance value exceeding a threshold or following one or more loops of steps 101, 103, 105 and 115 that do not result in the required performance being achieved), the control unit can then perform steps 109 and 111 and notify the user of the nebulizer 2 that the nebulizing element 16 needs to be manually repositioned in the nebulizer 2.

It will also be appreciated that a control unit 18 can be provided that can implement both of the embodiments shown in FIGS. 6C and 6D. In this case, when the control unit 18 determines that the nebulizing element 16 is not positioned correctly in the nebulizer 2, the control unit 18 can adjust both the frequency of vibration of the piezoelectric element 14 and the position of the nebulizing element 16 in the nebulizer 2 in order to improve the droplet generation performance of the nebulizer 2.

Referring again to FIG. 3B, it will be noted that the maximum droplet generation rate for a piezoelectric element 14 operating at a frequency f is obtained with a separation of $h_f$, and the piezoelectric element 14 has an impedance $Z_f$. As described in the embodiments above, it is possible to determine whether the nebulizing element 16 is positioned correctly by measuring the impedance of the piezoelectric element 14 and comparing it to the optimal value (i.e. $Z_f$). However, it will be noted from FIG. 3B that the 'optimal' impedance value $Z_f$ actually corresponds to two possible distances, $h_f$ and $h_f'$, between the piezoelectric element 14 and nebulizing element 16.

Now, it may be that the second possible distance $h_f'$ cannot occur in the nebulizer 2 (for example $h_f'$ may be greater than the dimensions of the reservoir chamber 10) in which case the possibility that the nebulizing element 16 and piezoelectric element 14 are separated by this distance ($h_f'$) can be ignored in the implementation of the method illustrated in FIG. 6A.

However, it is also possible that the second possible distance $h_f'$ can occur, in which case executing the method shown in FIG. 6A could result in a false-positive result (i.e. the control unit 18 may determine that the nebulizing element 16 is positioned correctly, when it is not). Therefore, an alternative method of operating a nebulizer 2 is presented in FIG. 7.

In step 201, the piezoelectric element 14 is operated at a first frequency of vibration. In some cases, this may be frequency f, i.e. the frequency at which the best droplet generation performance is obtained (note the different maximum droplet generation rates for the different frequencies of vibration in FIG. 3A).

Then, in step 203, the impedance of the piezoelectric element 14 is measured. This measurement step can be carried out in the same way as step 101 in FIG. 6A.

The control unit 18 then determines whether the measured impedance is equal to or within a predetermined range of a desired impedance value for the first frequency f (i.e. $Z_f$) in step 205. If not, the control unit 18 can proceed as shown in any of FIGS. 6B, 6C and 6D described above, with the process returning to step 201 if the impedance needs to be remeasured.

If the measured impedance is equal to or close to the desired impedance value $Z_f$, the control unit 18 operates the piezoelectric element 14 at a second frequency of vibration different to the first frequency (step 207), for example f+Δf or f−Δf shown in FIGS. 3A and 3B and re-measures the impedance of the piezoelectric element 14 (step 209). In one embodiment, the second frequency can differ from the first frequency by around 0.2%, although it will be appreciated the smaller and larger frequency differences can be used.

In step 211, the control unit 18 determines whether the impedance value measured in step 209 is equal to or within a predetermined range of an impedance value appropriate for the second frequency and the separation $h_f$. For example, if the second frequency is f+Δf, the control unit 18 determines whether the impedance value measured in step 209 is equal to or within a predetermined range of $Z_{f+\Delta f}$.

If the impedance value measured in step 209 is within the predetermined range of the impedance value appropriate for the second frequency and separation $h_f$, the control unit 18 can initiate or continue operation of the nebulizer 2 (step 213). If not, the control unit 18 can proceed as shown in any of FIGS. 6B, 6C and 6D described above, with the process returning to step 201 if the impedance needs to be remeasured.

Those skilled in the art will appreciate that it is possible to implement variations of the method shown in FIG. 7. For example, the measurements of the impedances at both of the operating frequencies (steps 203 and 207 in FIG. 7) can be carried out before any comparison with the respective predetermined impedance values (steps 205 and 211 in FIG. 7).

There is therefore provided a control unit for a nebulizer and a method of controlling a nebulizer that can detect whether the nebulizing element has been positioned correctly. In addition, specific embodiments of the invention provide a control unit and method that can improve the performance of the nebulizer in the event that it is determined that the nebulizing element has not been positioned correctly.

It will also be appreciated that, in addition to the control unit described above, the invention can be provided in the form of a computer program carried on a computer readable medium that is configured to cause a processor in a control unit for a nebulizer to execute the steps shown in FIG. 6A and any of FIGS. 6B-6D.

Those skilled in the art will appreciate that the word "nebulizer" can be used interchangeably with the term drug delivery apparatus or atomizer, and the use of the word "nebulizer" is intended to cover forms and designs of nebulizer other than the specific type of nebulizer described above and illustrated in the Figures.

While the invention has been illustrated and described in detail in the drawings and foregoing description, such illustration and description are to be considered illustrative or exemplary and not restrictive; the invention is not limited to the disclosed embodiments.

Variations to the disclosed embodiments can be understood and effected by those skilled in the art in practicing the claimed invention, from a study of the drawings, the disclosure and the appended claims. In the claims, the word "comprising" does not exclude other elements or steps, and the indefinite article "a" or "an" does not exclude a plurality. A single processor or other unit may fulfill the functions of several items recited in the claims. The mere fact that certain measures are recited in mutually different dependent claims does not indicate that a combination of these measures cannot be used to advantage. A computer program may be stored/distributed on a suitable medium, such as an optical storage medium or a solid-state medium supplied together with or as part of other hardware, but may also be distributed in other forms, such as via the Internet or other wired or wireless telecommunication systems. Any reference signs in the claims should not be construed as limiting the scope.

The invention claimed is:

1. A control unit for controlling the operation of a nebulizer, wherein the control unit is configured to measure the impedance of an actuator in the nebulizer and to determine whether a nebulizing element in the nebulizer is positioned correctly with respect to the actuator based on the measured impedance, the measured impedance being a function of a distance between the nebulizing element and the actuator, and wherein the determination of whether the nebulizing element is positioned correctly with respect to the actuator is based upon the distance being within a predetermined distance range,
the nebulizing element being configured to generate droplets of liquid, and
the nebulizing element comprising a membrane having a plurality of holes through which the droplets of liquid pass.

2. A control unit as claimed in claim 1, wherein the control unit is configured to determine that the nebulizing element is positioned correctly responsive to the measured impedance of the actuator being within a predetermined impedance range.

3. A control unit as claimed in claim 1, wherein the control unit is configured to measure the impedance of the actuator when the actuator is operating at first and second frequencies, and to determine that the nebulizing element is positioned correctly responsive to both of the measured impedances being within a predetermined impedance range.

4. A control unit as claimed in claim 1 wherein the control unit is further configured to activate the actuator to nebulize liquid responsive to a determination that the nebulizing element is positioned correctly in the nebulizer.

5. A control unit as claimed in claim 1, wherein the control unit is further configured to deactivate the actuator responsive to a determination that the nebulizing element is not positioned correctly.

6. A control unit as claimed in claim 5, wherein the control unit is further configured to provide an indication to a user of the nebulizer that the nebulizing element needs to be repositioned by the user.

7. A control unit as claimed in claim 1, wherein the control unit is further configured to adjust a frequency of vibration of the actuator responsive to a determination that the nebulizing element is not positioned correctly.

8. A control unit as claimed in claim 1, wherein the control unit is further configured to adjust the relative position of the actuator and the nebulizing element using a second actuator in the nebulizer responsive to a determination that the nebulizing element is not positioned correctly.

9. A control unit as claimed in claim 8, wherein the control unit is further configured to re-measure the impedance of the actuator after the adjustment.

10. A control unit as claimed in claim 1, wherein the control unit is configured to measure the impedance of the actuator by:
   (i) applying a sinusoidal voltage with a known amplitude to the actuator and measuring the amplitude of the resulting current and the phase shift between the resulting current and the applied voltage; or
   (ii) measuring the voltage across the actuator and current through the actuator during operation.

11. A method of controlling a nebulizer, the method comprising:
measuring the impedance of an actuator in the nebulizer; and determining whether a nebulizing element in the nebulizer is positioned correctly with respect to the actuator based on the measured impedance and whether a distance between the nebulizing element and the actuator is within a predetermined distance range, wherein
   the nebulizing element is configured to generate droplets of liquid, and
   the nebulizing element comprises a membrane having a plurality of holes through which the droplets of liquid pass.

12. A method as claimed in claim 11, wherein the nebulizing element is determined to be positioned correctly if the measured impedance of the actuator is equal to or within a predetermined range of a predetermined impedance value.

13. A method as claimed in claim 11, wherein the step of measuring the impedance of the actuator comprises measuring the impedance of the actuator at first and second frequencies, and wherein the step of determining comprises determining that the nebulizing element is positioned correctly if both of the measured impedances are equal to or within a predetermined range of respective predetermined impedance values.

14. A computer program product comprising a computer readable medium having computer program code embodied therein, the computer program code comprising code that, when executed by a computer or processor, is configured to cause the computer or processor to perform the steps in the method according to claim 11.

* * * * *